(12) United States Patent
Sullivan, III et al.

(10) Patent No.: US 6,238,402 B1
(45) Date of Patent: May 29, 2001

(54) PULL BACK STENT DELIVERY SYSTEM WITH PISTOL GRIP RETRACTION HANDLE

(75) Inventors: Roy Sullivan, III, Millville; Robert B. DeVries, Marlborough, both of MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/365,482

(22) Filed: Aug. 2, 1999

Related U.S. Application Data

(62) Division of application No. 08/753,641, filed on Nov. 27, 1996, now Pat. No. 5,968,052.

(51) Int. Cl.⁷ ........................................................ A61F 11/00
(52) U.S. Cl. ........................................................ 606/108
(58) Field of Search ............................. 606/108, 198, 606/194, 1, 192, 195, 191; 604/96, 101

(56) References Cited

U.S. PATENT DOCUMENTS

| | | |
|---|---|---|
| 5,160,341 | 11/1992 | Brenneman et al. . |
| 5,209,730 | 5/1993 | Sullivan ................................. 604/96 |
| 5,415,664 | 5/1995 | Pinchuk . |
| 5,433,723 | 7/1995 | Lindenberg et al. . |
| 5,464,408 | 11/1995 | Duc . |
| 5,639,274 | * 6/1997 | Fischell et al. ........................ 604/96 |
| 5,980,531 | * 11/1999 | Goodin et al. ....................... 606/108 |
| 5,989,280 | * 11/1999 | Euteneuer et al. ................... 606/198 |

FOREIGN PATENT DOCUMENTS

| | | |
|---|---|---|
| 0 518 838 A1 | 6/1992 | (EP) . |
| 0 627 201 A1 | 6/1993 | (EP) . |
| WP 9521593 | 8/1995 | (WO) . |

* cited by examiner

*Primary Examiner*—Kevin Truong
(74) *Attorney, Agent, or Firm*—Vidas, Arrett & Steinkraus

(57) ABSTRACT

A stent delivery system for delivering a self-expanding stent to a predetermined location in a vessel includes a catheter body having an axial guidewire lumen and a pull-wire lumen. A medical device such as a self-expanding stent is held in a reduced delivery configuration for insertion and transport through a body lumen to a predetermined site for deployment. The stent is carried axially around the catheter body near its distal end and held in its reduced configuration by a retractable outer sheath. A proximal retraction handle is connected to the proximal end of the catheter body and includes a pistol grip trigger engaging a rachet mechanism, which is connected to a pull-wire which extends through the pull-wire lumen and is connected to the retractable outer sheath.

1 Claim, 7 Drawing Sheets

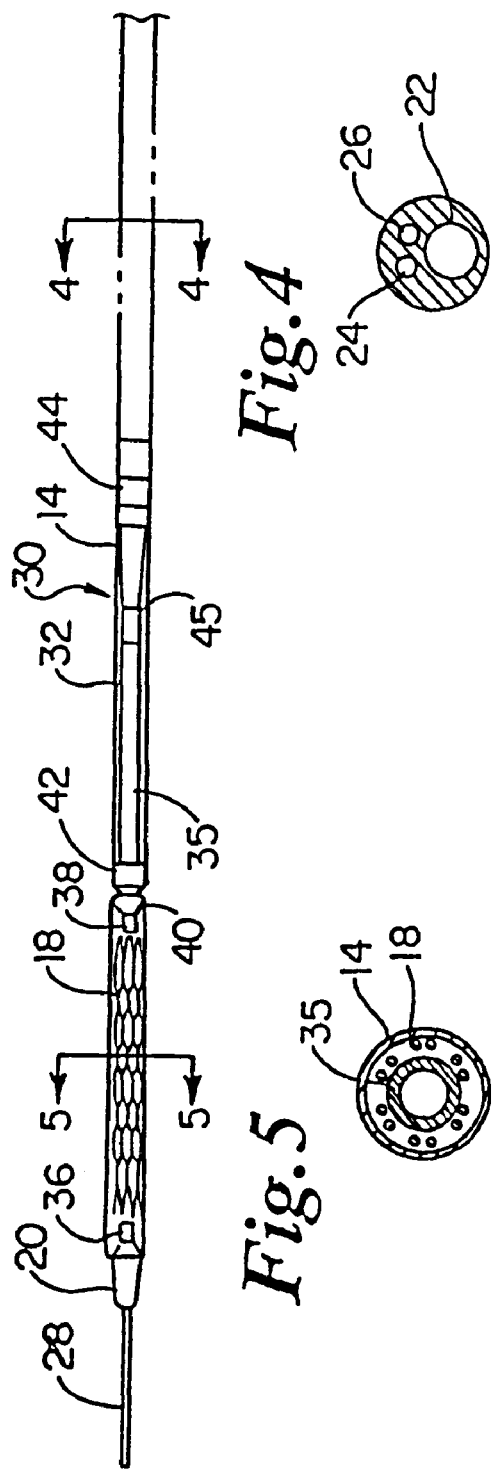
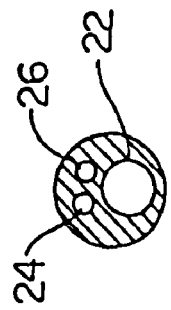
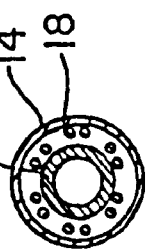
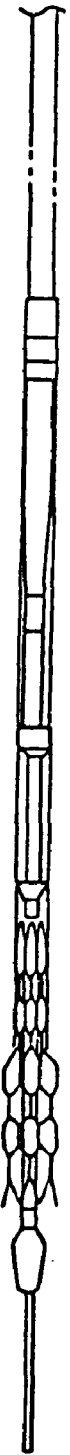

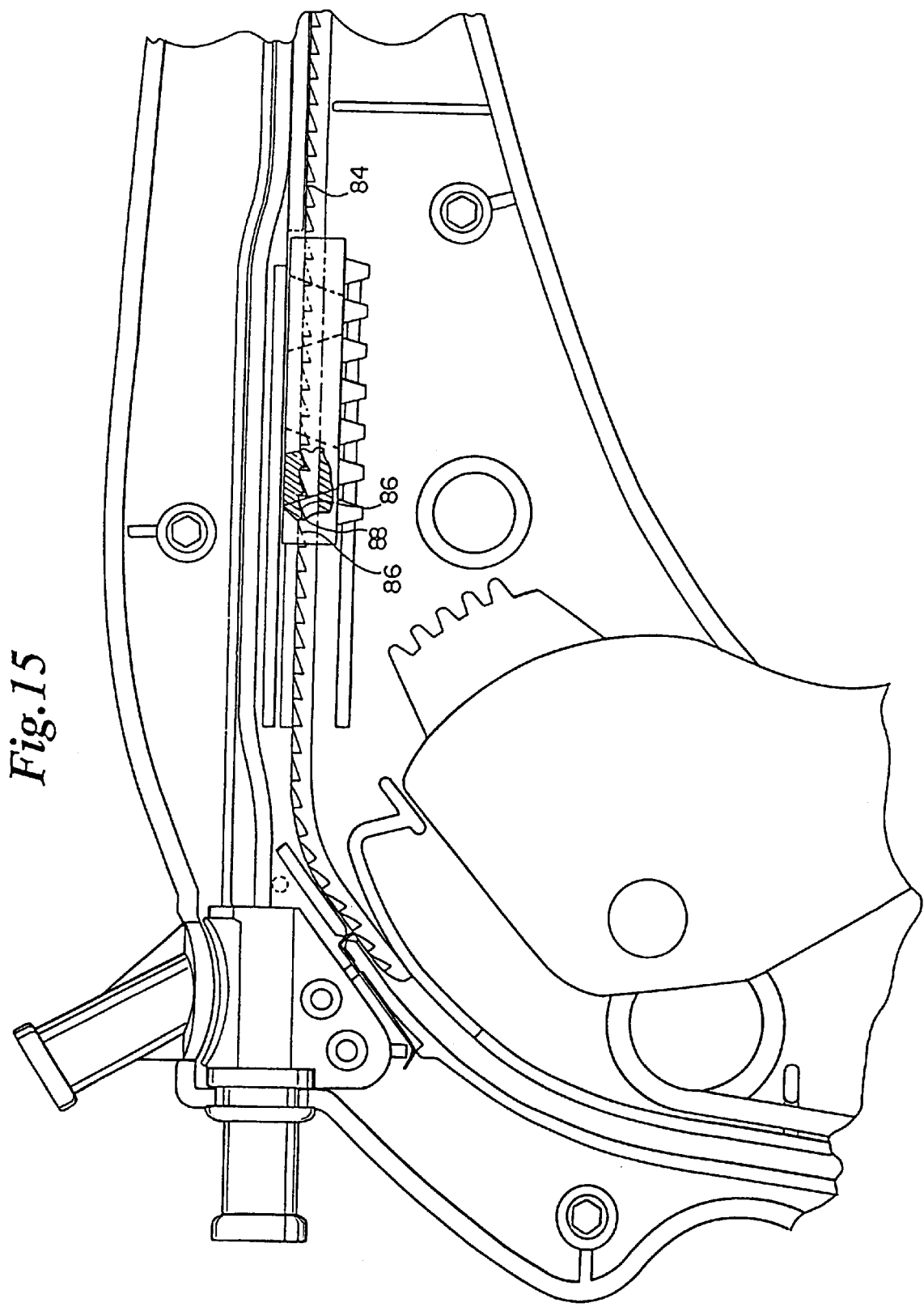

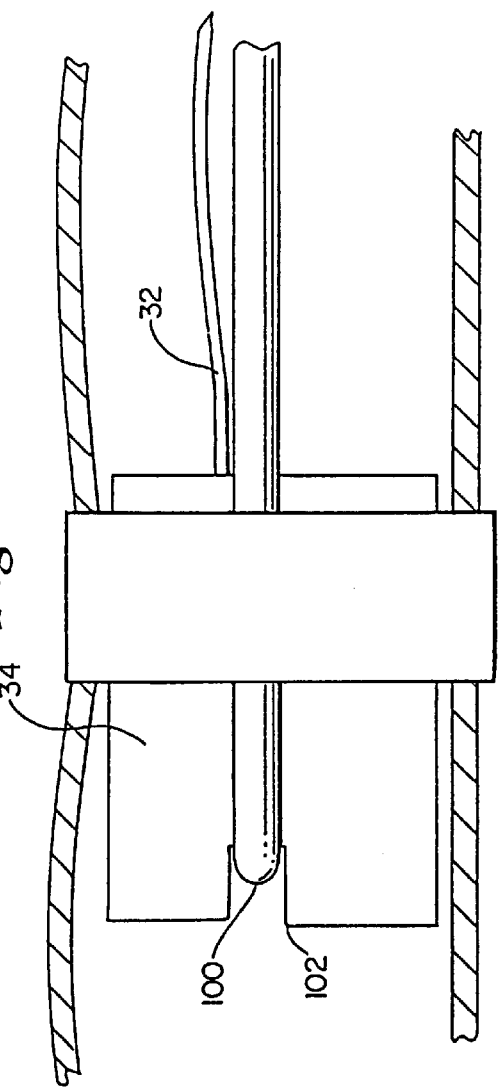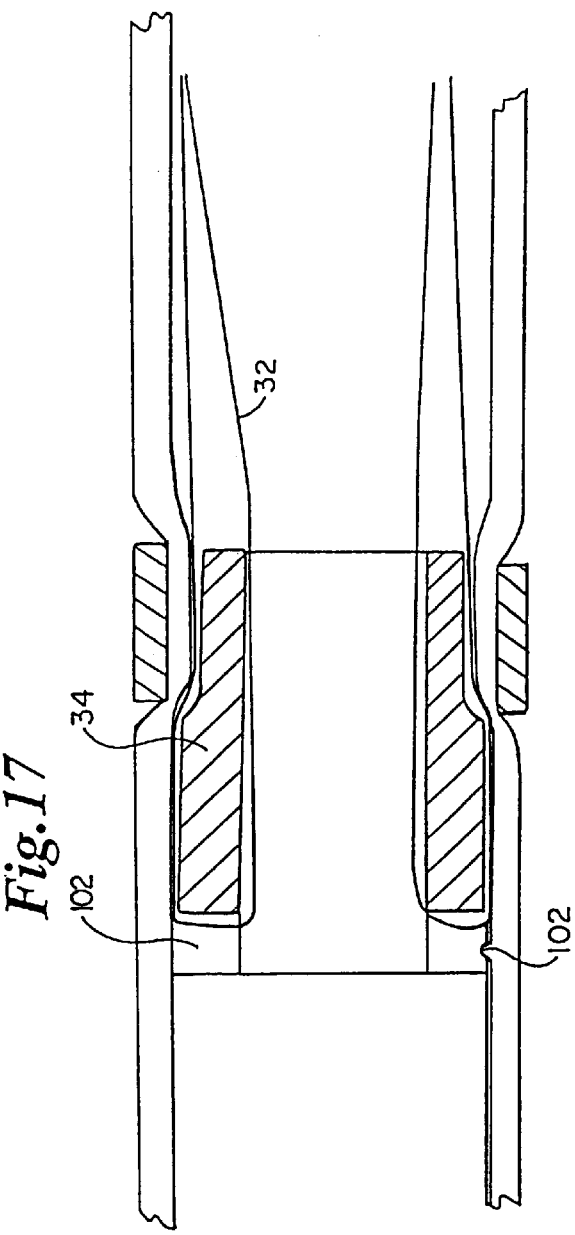

PULL BACK STENT DELIVERY SYSTEM WITH PISTOL GRIP RETRACTION HANDLE

CROSS-REFERENCE TO RELATED APPLICATIONS

This application is a Divisional application of application Ser.No. 08/753,641, filed Nov. 27, 1996, now U.S. Pat. No. 5,968,052 the entire contents of which are hereby incorporated by reference.

BACKGROUND OF THE INVENTION

1. Field of the Invention

The present invention relates to an improved wire pull back delivery system. More specifically, the invention relates to a wire pull-back stent delivery system which utilizes a pistol grip retraction handle to retract the retractable outer sheath and deploy a medical implant for a minimally invasive application, such as an endovscular stent graft, vena cava filter, self-expanding stent, balloon expandable stent, or the like.

2. Description of the Related Art

Delivery system for deploying medical implants, such as an endovscular stent graft, vena cava filter, self-expanding stent, balloon expandable stent or the like, are a highly developed and well known field of medical technology. These medical devices have many well known uses and applications. In particular, a stent is a prosthesis which is generally tubular and which is expanded radially in a vessel or lumen to maintain its patency. Stents are widely used in body vessels, body canals, ducts or other body lumens. A self-expanding stent is a stent which expands from a compressed delivery position to its original diameter when released from the delivery device, exerting radial force on the constricted portion of the body lumen to re-establish patency. One common self-expanding stent is manufactured of Nitinol, a nickel-titanium shape memory alloy, which can be formed and annealed, deformed at a low temperature, and recalled to its original shape with heating, such as when deployed at body temperature in the body.

Wire pull-back stent delivery systems are disclosed in U.S. Pat. No. 5,360,401 and U.S. Pat. No. 5,571,135. One important factor in delivering the stent is a controlled precise retraction of the retractable outer sheath. What is needed is a wire pull-back stent delivery system which provides for a controlled and precise retraction of the retractable outer sheath and enables the physician to accurately determine proper positioning of the stent, as well as track the retraction of the outer sheath.

SUMMARY OF THE INVENTION

The inventive stent delivery system for delivering a self-expanding stent to a predetermined location in a vessel includes a catheter body having an axial guidewire lumen and a pull-wire lumen. A medical device such as a self-expanding stent is held in a reduced delivery configuration for insertion and transport through a body lumen to a predetermined site for deployment. The stent is carried axially around the catheter body near its distal end and held in its reduced configuration by a retractable outer sheath. A proximal retraction handle is connected to the proximal end of the catheter body and includes a pistol grip trigger engaging a rachet mechanism, which is connected to a pull-wire which extends through the pull-wire lumen and is connected to the retractable outer sheath.

BRIEF DESCRIPTION OF THE DRAWINGS

A detailed description of the invention is described below with specific reference being made to the drawings, in which:

FIG. 3 shows the distal end of the inventive stent delivery system;

FIG. 4 is a cross-sectional view of the catheter body taken along section line 4—4 of FIG. 3;

FIG. 5 is a cross-sectional view of the catheter body taken along section line 5—5 of FIG. 3;

FIGS. 13 and 14 show the delivery system partially and fully deployed;

FIG. 15 shows the flexible ratcheting pawl in more detail, and

FIGS. 16 and 17 show an alternate embodiment for attaching the pullwire to the pull-ring.

DESCRIPTION OF THE PREFERRED EMBODIMENT

Figure 1:
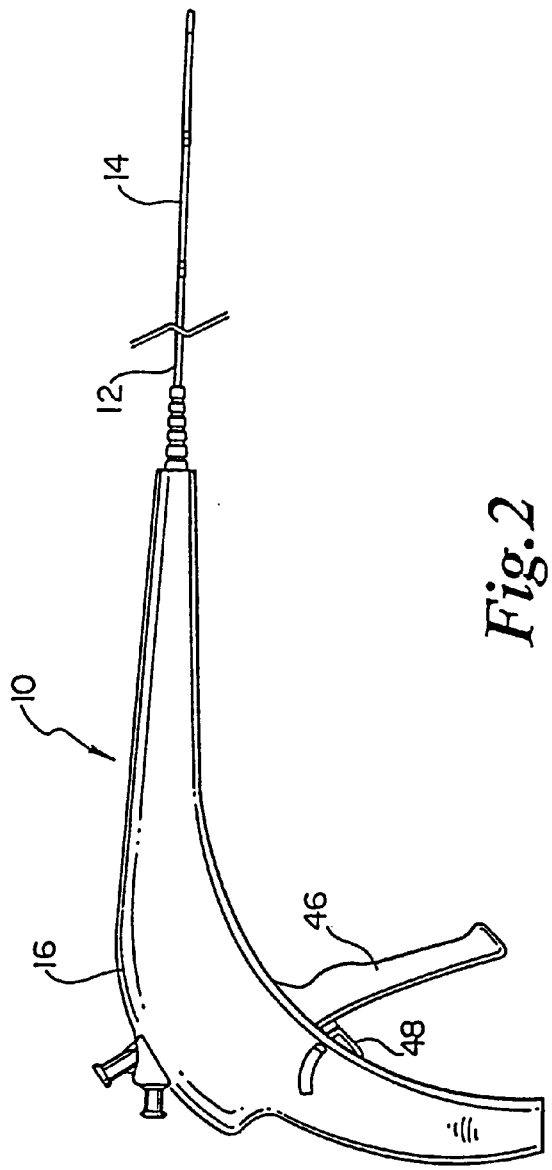
FIGS. 1 and 2 are side views of the inventive stent delivery system.

While this invention may be embodied in many different forms, there are shown in the drawings and described in detail herein a specific preferred embodiment of the invention. The present disclosure is an exemplification of the principles of the invention and is not intended to limit the invention to the particular embodiment illustrated.

Figure 2:
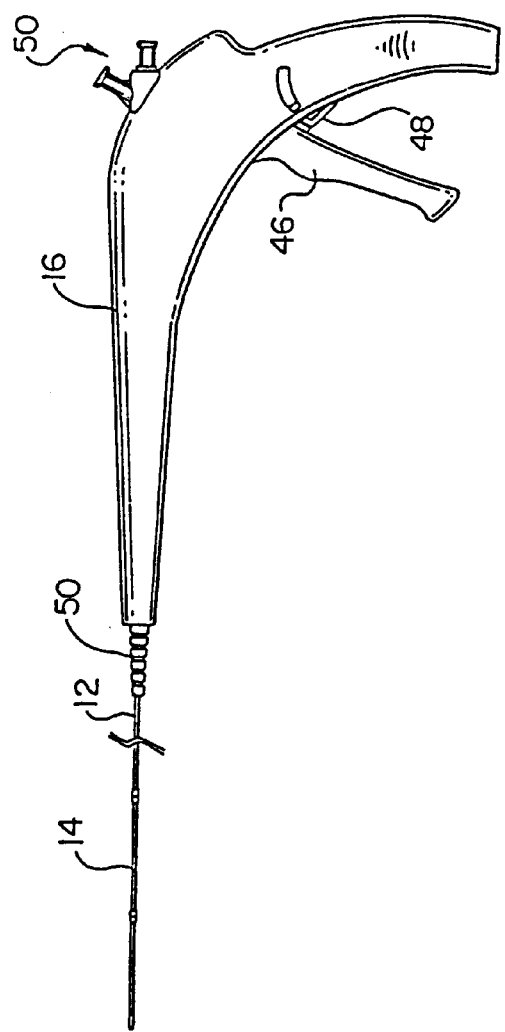

FIGS. 1 and 2 show side views of the inventive delivery system. The preferred embodiment discussed below specifically discusses delivering a self-expanding stent, but it should be understood that the inventive delivery system can deliver any medical implant for a minimally invasive application, such as an endovascular stent graft, vena cava filter, self-expanding stent, balloon expandable stent or the like.

The preferred embodiment is a two-part system including an implantable medical device such as a self-expanding stent and a delivery catheter. The delivery catheter is shown generally at 10 and includes the catheter body 12, the retractable outer sheath 14 and the proximal retraction handle 16.

FIG. 3 shows the distal end of the delivery system 10, and the retractable outer sheath 14 in more detail. A medical device is held in its delivery configuration by outer sheath 14, and in the preferred embodiment the medical device is a self-expanding stent 18 which is carried concentrically around the single lumen extrusion 35 near the distal tip 20.

FIG. 4 shows that catheter body 12 is a tri-lumen catheter, and in the preferred embodiment is a nylon extrusion with a guidewire lumen 22, a stent flushing lumen (priming port) 24 and a pull-wire lumen 26. The guidewire lumen accommodates a 0.035 inch guidewire 28. The guidewire lumen 22 and stent flushing lumen 24 terminate at the point shown generally at 30, and a stainless steel pull-wire 32 is shown extending from the pull-wire lumen 26 and which attaches to a stainless steel ring 34 (best seen in FIG. 6). A nylon single lumen (guidewire lumen) extrusion 35 is thermally lap welded to the catheter body 12 at point 30 and has a nylon extrusion which is thermally molded to the distal end of the nylon single guidewire lumen 35 and tapered to create smooth atraumatic tip 20.

FIG. 5 shows a cross-section view of the single guidewire lumen extrusion 35 along section lines 5—5 of FIG. 3.

In the preferred embodiment, tantalum radiopaque marker bands 36 and 38 are bonded to the single lumen extrusion 35 using cyanoacrylate adhesive, although it should be understood that marker bands 36 and 38 could be attached using other well known techniques such as weld swaging or crimp/swaging. Marker bands 36 and 38 are used in connection with an imaging procedure to aid in determining proper positioning of the stent in the body lumen. Although fluoroscopy is the most common imaging procedure typically employed, x-ray, MRI or any other well known imaging techniques may also be utilized. In the embodiment of FIG. 3 marker bands 36 and 38 show the proximal and distal ends of the stent 18 as carried in its delivery configuration. An alternate embodiment may locate marker bands 36 and 38 to mark the proximal and distal ends of the stent 18 in its expanded position, which would have a slightly shorter length than the stent in its delivery configuration. A nylon band stent stop 40 is also bonded to the single lumen extrusion 35 and prevents the stent 18 from moving proximally along the single lumen extrusion 35 as the outer sheath 14 retracts, assisting in accurate stent placement. Stop 40 could also be attached using any standard technique, such as overmolding or ultrasonic welding.

In the preferred embodiment the retractable outer sheath 14 is a clear medical grade PTFE (polytetrafluoroethylene) extrusion which covers the distal 10–20 cm (depending on stent length) of the catheter body 12. However the outer sheath 14 could be made of any suitable fluropolymer material. A specific alternate embodiment could utilize a fluropolymer material which is transparent to visible light to enable the operator to directly view deployment in an endoscopic delivery procedure. Such materials are well known in the art. In the preferred embodiment self-expanding nitinol stents of from 6–14 mm in diameter and ranging from 20–100 mm in length can be accommodated. It should be understood that any type of self-expanding stent could be employed, although nitinol self-expanding stents are preferred. The retractable outer sheath 14 is connected to the proximal retraction handle 16 by stainless steel pull-wire 32 which is welded to stainless steel ring 34 (best seen in FIG. 6). Ring 34 is swaged in place to the outer sheath 14 with tantalum radiopaque marker band 42. The distal end of retractable outer sheath 14 is designed to flush fit with tip 20 to create a smooth profile. The proximal end of retractable outer sheath 14 is finished with a smooth transition consisting of a thermally molded nylon extrusion swaged in place with a tantalum radiopaque marker band 44 (best seen in FIG. 7). It should be understood that tapered transition could be molded in place, which would eliminate the need for a marker band swaged in place to attach the nylong extrusion. It should also be understood that the marker band could be bonded or crimp/swaged. The tapered smooth transition of the proximal portion of outer sheath 14 allows catheter body 12 to be more easily extracted from the body lumen and introducer sheath. The proximal end of retractable outer sheath 14 slidably seals to catheter body 12 permitting it to slide proximally along catheter body 12 when retracted by pull-wire 32. The nitinol stent 18 is compressed at low temperature for loading into delivery system 10 and held in its reduced delivery configuration by retractable outer sheath 14. Upon deployment in vivo at body temperature the original stent shape is restored as the nitinol stent self-expands, exerting radial force on the constricted portion of the body lumen to re-establish patency. Marker band 45 is also bonded to extrusion 35 approximately one stent length proximally of marker band 42 (in the unretracted position) and is utilized to confirm full stent release as discussed further below. It should be understood that marker band 45 could also be attached using swaging or crimp/swaging.

Figure 6:
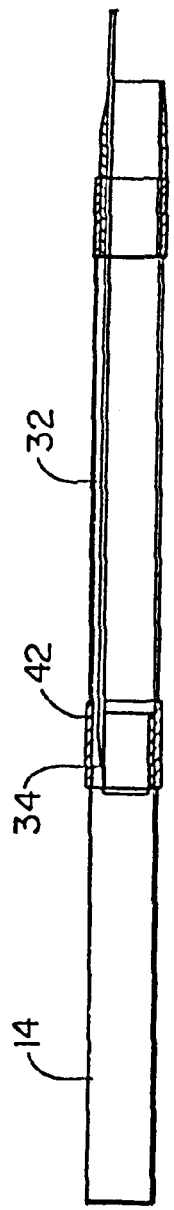
FIGS. 6–8 show details of FIG. 3 in greater detail.
Figure 7:
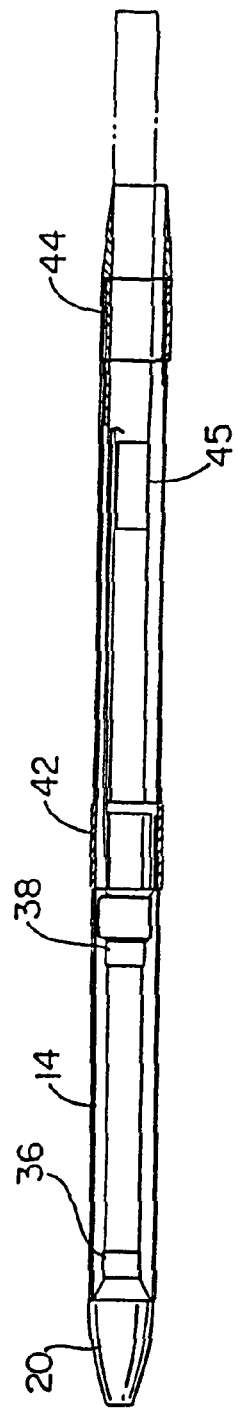
Figure 8:

FIGS. 6–8 show details of FIG. 3 is more detail.

Referring again to FIGS. 1 and 2, the stent 18 is deployed using proximal retraction handle 16. Proximal retraction handle 16 is a multi-component assembly ergonomically designed with a pistol grip trigger 46. The trigger mechanism 46 is contained within a two-part molded ABS (acrylonitrile, butadiene, styrene) outer housing that is snap-fit together. The ABS trigger 46 has a polypropylene safety lock mechanism 48 to prevent inadvertent stent release. The proximal retraction handle 16 is connected to the catheter body 12 by the pull-wire 32, a Y-luer assembly shown generally at 50 and a strain relief 52.

Figure 9:
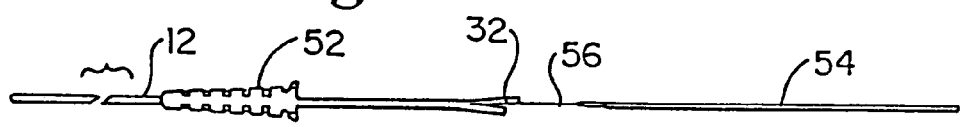
FIG. 9 shows the connection of the pull-wire to the strip portion of the rachet mechanism.

Referring now to FIG. 9, catheter body 12 is connected to strain relief 52, and the proximal end of pull-wire 32 exits from lumen 26 and is threaded and crimped to a strip 54 by crimp tube 56, which is part of the ratchet mechanism used to retract outer sheath 14. Strain relief 52 is made of Pebax® and is insert molded over catheter body 12, and is constructed to fit inside the nose of proximal handle 16 (best seen in FIGS. 11 and 12).

Figure 10:
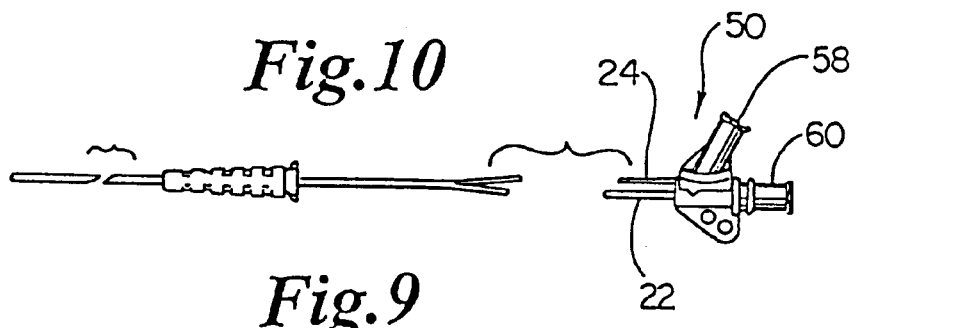
FIG. 10 shows the Y-luer.

Referring now to FIG. 10, the Y-luer assembly 50 is shown, and consists of a nylon Y-luer with a nylon single lumen extrusion overmolded to each leg of the "Y". It should be understood that the extrusion could also be bonded to each leg of the "Y". Leg 58 of the "Y" forms the stent flushing port and leg 60 forms the guidewire port. Each single lumen is thermally lap welded to the catheter body 12 and provides communication between the Y-luer and the guidewire lumen 22 and the stent flushing lumen 24. The stent flushing lumen is used to fill the retractable outer sheath 14 with fluid to purge air out of the outer sheath 14 prior to insertion of the catheter body 12 into the body.

Figure 11:
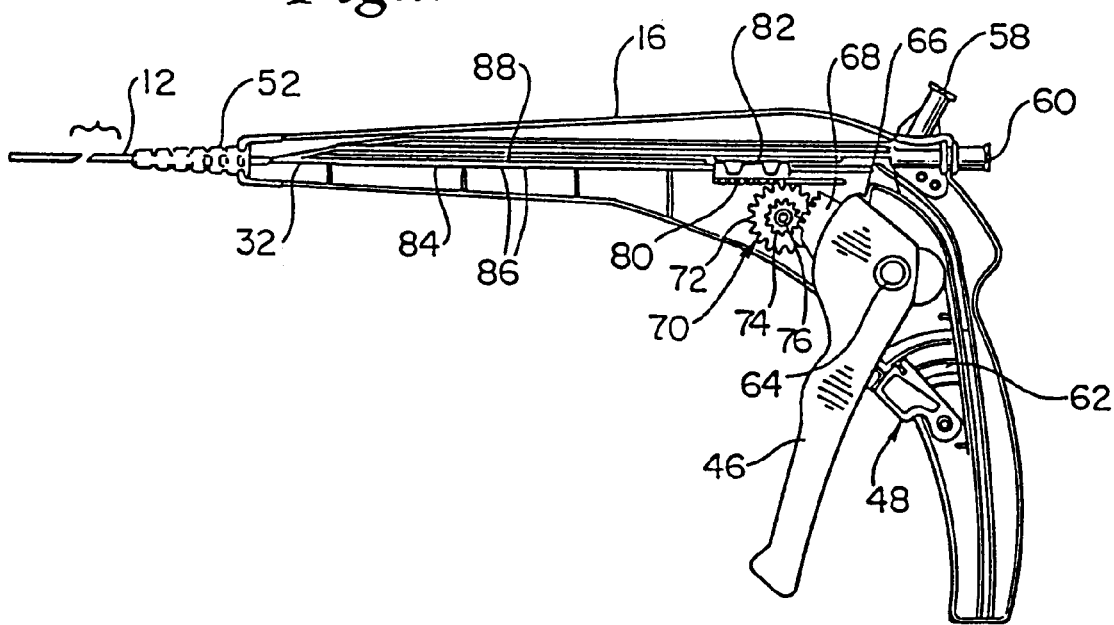
FIG. 11 shows one side of the two-piece snap fit proximal retraction handle with its components in place.

Referring now to FIG. 11, the proximal retraction handle 16 is shown in more detail and is a multi-component assembly ergonomically designed with a pistol grip 46, which is engaged by trigger spring 62. The pistol grip 46 or trigger has two cylindrical protrusions 64 on either side of trigger 46 which extend outwardly and are received by pivot mounts molded into the proximal retraction handle 16 to attach the pistol grip 46 to the handle 16 as well as provide a point about which the pistol grip rotates. A trigger stop 66 defines the normal trigger position and the trigger 46 is maintained in this normal position by trigger spring 62. As the trigger 46 is squeezed it rotates to its compressed position, and when released the trigger spring forces the trigger to rotate back to its normal position flush with the trigger stop 66. Trigger 46 includes a pair of gear engaging members 68 which are spaced apart to form a channel wide enough to receive the larger gear 72 of gear 70. Gear 70 includes gear 72 and a pair of gears 74 fixedly attached on either side of gear 72. Gears 74 engage the gear engaging portions 68 of trigger 46 to rotate gear 70 as trigger 46 rotates. Axle 76 is received by molded mounts in the two parts of handle 16 to attach the gear to the handle 16. Gear 72 engages the ratchet mechanism which is attached to the pull-wire 32. The ratchet mechanism is comprised of a rack driver which is comprised of 2 parts, a rack 80 and a rack tab 82, which snap fit together to form a channel for receiving strip 84. As can be seen best in FIG. 15, strip 84 contains ramp shaped stops 86, each adjacent pair of stops forming detents 88 (best seen in FIG. 15). Rack tab 82 contains a flexible ratcheting pawl 89 which engages with detents 88 such that when the rack driver is moved proximally when the trigger 46 is squeezed to its compressed position, strip 84 is moved proximally, but when the rack driver is moved distally when trigger 46 is rotated to its normal position, the flexible ratcheting pawl 89 slides up ramp shaped stop 86 to disengage from strip 84.

Figure 12:
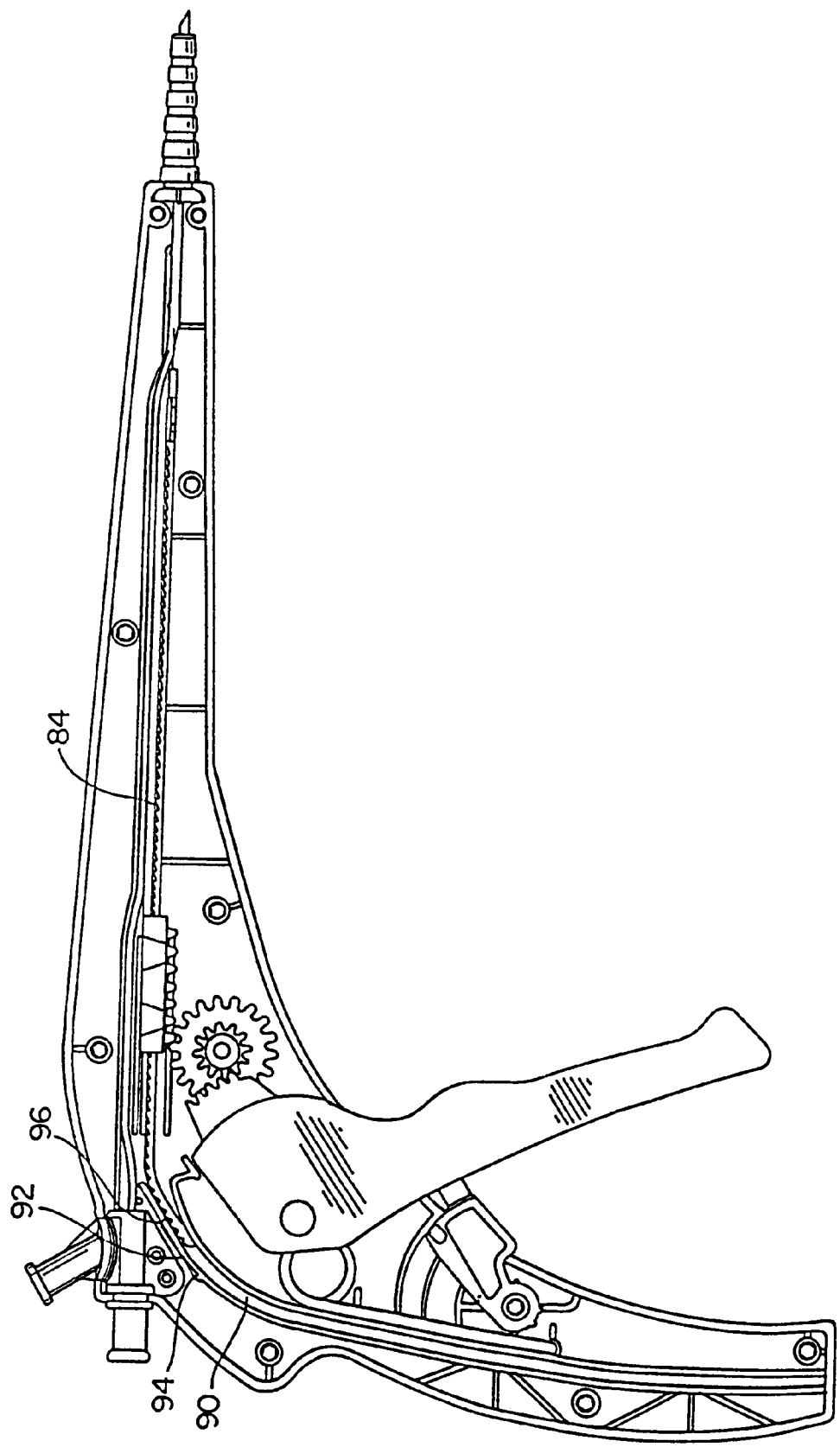
FIG. 12 shows the other side of the two-piece snap fit proximal retraction handle with the strip retracted into a channel.

As is best shown in FIG. 12, strip 84 is received by channel 90. A second spring, strip spring 92 is securely held to handle 16 by tail 94 and its locking head portion 96 lockingly engages with detents 88 to hold strip 84 in place when trigger 46 is released and rack tab 82 is moved distally to lockingly engage with the adjacent distal detent 88. The ramp shaped stops 86 (best seen in FIG. 15) allow the strip to be moved proximally in channel 90 by rack tab 82 until the adjacent detent lockingly engages with strip spring 92. The detents are each approximately 2 mm apart so that each complete squeeze of the trigger 46 retracts the pull-wire 32 and outer sheath 14 approximately 20 mm. By repeatedly squeezing and releasing trigger 46 the outer sheath 14 is fully retracted to release the stent 18 to self-expand. The rachet mechanism is designed to work with any stent of lengths between 20 and 100 mm, although it could easily be designed to accept any desired length stent.

The ratio of gear 70 in the embodiment shown in FIG. 12 is 2:1, such that a 1 mm squeeze on trigger 46 retracts the outer sheath 2 mm. However, it should be understood that any desired gear ratio could be utilized. For example gear 70 is designed optionally to allow for a gear ratio of 1:1. In that embodiment a trigger 46 with a single gear engaging portion 68 is designed to engage gear 72, rather than gears 74, to provide a 1:1 ratio such that a 1 mm squeeze on the trigger will retract the outer sheath 14 1 mm. In order to accommodate this detents 88 would be spaced approximately 1 mm apart on strip 84 and it should be understood that the stops 86 and detents 88 could be arranged in any desired spacing. Gear 70 could also be designed if desired to have a ratio of 1:2, such that a 2 mm squeeze of trigger 46 retracts outer sheath 14 1 mm.

In operation, pre-placement imaging or other standard procedure is normally performed to identify an insertion tract and assess the site. A guidewire (0.035 inch diameter in the preferred embodiment) 28 is maneuvered through the tract. The delivery system 10, with the preloaded medical device (a self-expanding stent in the preferred embodiment) is then passed through an introducer sheath and tracked over the guidewire until the medical device is positioned as desired. In the preferred embodiment markers 36 and 38 are used with standard imaging techniques such as fluoroscopy, x-ray, MRI or the like to aid in proper positioning of the stent 18 across the stricture. As the trigger 46 is repeatedly squeezed, the outer sheath 14 is retracted proximally to release the stent to self-expand. To aid in confirming complete stent deployment and release the operator observes marker 42 move to meet marker 45.

FIGS. 3, 13 and 14 show the distal end of delivery system 10 in a pre-deployed state (FIG. 3), partially deployed state (FIG. 13) and fully deployed state (FIG. 14).

Referring now to FIGS. 16 and 17, an alternate embodiment of the inventive delivery system is shown where the pull-wire 32 is U-shaped with the U loop portion 100 of the pull-wire 32 looping around a notch 102 in the pull-ring 34. The 2 ends of the U-shaped pull-wire extend through pull-wire lumen 26 to attach to the ratchet mechanism. As shown in FIG. 17, if desired a plurality of pull-wires 32 could by looped around a plurality of notches 102 spaced around pull-ring 34. A second pull-wire lumen could be provided to carry one or more pull-wires 32 to allow the pull-ring to be retracted with the pulling force more evenly distributed around the pull-ring perimeter. Two U-shaped pull-wires 32, each carried by a separate lumen and each looping around pull-ring 34 as shown in FIG. 17 would provide 4 points arranged around pull-ring 34 to more evenly distribute the pulling force on the pull-ring. Each pull-wire lumen could also optionally carry more than 1 pull-wire to provide as many attachment points on pull-ring 34 as desired.

This completes the description of the preferred and alternate embodiments of the invention. It is to be understood that even though numerous characteristics and advantages of the present invention have been set forth in the foregoing description, together with the details of the structure and function of the invention, the disclosure is illustrative only and changes may be made in detail, especially in matters of shape, size and arrangement of parts within the principals of the invention, to the full extent indicated by the broad, general meaning of the terms in which the appended claims are expressed. Those skilled in the art may recognize other equivalents to the specific embodiment described herein which are intended to be encompassed by the claims attached hereto.

What is claimed is:

1. A delivery system for delivering a medical device to a predetermined location in a body lumen, the delivery system comprising:

a catheter body having proximal and distal ends for transporting a medical device to a predetermined site in a body lumen for deployment;

a medical device having proximal and distal ends carried by the catheter body near the distal end;

a first radiopaque marker band positioned on the catheter body approximately the axial length of the medical device proximal to the medical device;

a retractable outer sheath having proximal and distal ends and surrounding the medical device and maintaining the medical device in a delivery configuration where the medical device has a reduced radius along its entire axial length;

the retractable outer sheath further including a second radiopaque marker band at its distal end;

wherein delivery of the medical device is confirmed by observing the second radiopaque marker band move to meet the first radiopaque marker band, indicating that the retractable outer sheath is fully retracted to deliver the medical device.

* * * * *